(12) United States Patent
Ingraham et al.

(10) Patent No.: US 6,794,158 B2
(45) Date of Patent: Sep. 21, 2004

(54) FLUORESCENCE POLARIZATION ASSAY

(75) Inventors: Richard Harold Ingraham, New Fairfield, CT (US); Mario G. Cardozo, Brookfield, CT (US); Christine Anne Grygon, Redding, CT (US); Rachel Rebecca Kroe, Bethel, CT (US); John Robert Proudfoot, Newtown, CT (US)

(73) Assignee: Boehringer Ingelheim Pharmaceuticals, Inc., Ridgefield, CT (US)

(*) Notice: Subject to any disclaimer, the term of this patent is extended or adjusted under 35 U.S.C. 154(b) by 230 days.

(21) Appl. No.: 10/109,433

(22) Filed: Mar. 28, 2002

(65) Prior Publication Data

US 2003/0082665 A1 May 1, 2003

Related U.S. Application Data (60) Provisional application No. 60/282,575, filed on Apr. 9, 2001.

(51) Int. Cl.$^7$ .......................... C12Q 1/34; C12Q 1/00; G01N 33/53
(52) U.S. Cl. .............................. 435/18; 435/4; 435/968
(58) Field of Search .................. 435/18, 4, 968

(56) References Cited

U.S. PATENT DOCUMENTS

| | | | |
|---|---|---|---|
| 4,476,228 A | 10/1984 | Huchzermeier et al. | 436/500 |
| 4,510,251 A | 4/1985 | Kirkemo et al. | 436/536 |
| 5,445,956 A | 8/1995 | Hammock et al. | 435/195 |
| 5,876,946 A | 3/1999 | Burbaum et al. | 435/7.1 |
| 5,916,760 A | 6/1999 | Goeddel et al. | 435/15 |
| 5,939,302 A | 8/1999 | Goeddel et al. | 435/194 |
| 5,955,496 A | 9/1999 | Hammock et al. | 514/473 |
| 6,046,165 A | 4/2000 | Laughon et al. | 514/12 |
| 6,150,415 A | 11/2000 | Hammock et al. | 514/588 |
| 6,287,774 B1 * | 9/2001 | Nikiforov | 435/6 |

FOREIGN PATENT DOCUMENTS

| | | |
|---|---|---|
| WO | WO 98/06261 A1 | 2/1998 |
| WO | WO 03/002555 A1 | 1/2003 |

OTHER PUBLICATIONS

Moghaddam et al, Biochim Biophys Acta, V.1290(3), pp327–339, Aug. 13, 1996,(Abstract Only).*

Miyamoto, et al; "Inhibition of Epoxide Hydrolases and Glutathione S–Transferases by 2–, 3–, and 4–Substituted Derivatives of 4'–Phenylchalcone and its Oxide 1"; Arch. Biochem. Biophys., 254: 203–213 (1987).

Dietze, et al; "Inhibition of Cytosolic Epoxide Hydrolase By trans–3–Phenylglycidols"; Biochem. Pharm. 42: 1163–1175 (1991).

Dietz, et al; "Inhibition of Epoxide Hydrolase From Human, Monkey, Bovine, Rabbit And Murine Liver By Trans–3–Phenylglycidols"; Comp. Biochem. Physiol., 104B. Nr. 2: 309–314 (1993).

Morisseau, et al; "Potent urea and Carbamate inhibitors of soluble epoxide hydrolases"; Proc. Natl. Acad. Sci., 96: 8849–8854 (1999).

(List continued on next page.)

Primary Examiner—Louise N. Leary
(74) Attorney, Agent, or Firm—Robert P. Raymond; Michael P. Morris; Philip I. Datlow (57) ABSTRACT

This invention is directed to a fluorescence polarization assay useful in the detection and evaluation of soluble epoxide hydrolase (sEH) inhibitors. This invention also relates to novel fluorescent probes used in the fluorescence polarization assay, and methods of manufacturing such fluorescent probes.

This fluorescent probe of the invention is a compound having the following formula (I):

$$\text{X-spacer-R}_1\text{-Y} \qquad (I)$$

wherein X is the radical of compound that binds to the active site of soluble epoxide hydrolase, Y is a fluorescent label, and "spacer" and $R_1$ are as defined herein.

31 Claims, 2 Drawing Sheets

OTHER PUBLICATIONS

Argiriadi, et al; "Binding of Alkylurea Inhibitors to Epoxide Hydrolase implicates Active Site Tyrosines in Substrate Activation*"; J. Biol. Chem., 275 (20) 15265–15270 (2000).

Nakagawa, et al; "3–D QSAR Analysis of Inhibition of Murine Soluble Epoxide Hydrolase (MsEH) by Benzoylureas, Arylureas, and their Analogues"; Bioorg. Med. Chem.. 8:2663–2673 (2000).

S. Gill, et al; "Radiometric Assays for Mammalian Epoxide Hydrolases and Glutathion S–Transferase"; Analyt. Biochem., 131:273–282 (1983).

R. N. Wixtrom an B. D. Hammock; "Membrane–Bound And Soluble–Fraction Epoxide Hydrolases"; Biochem. Pharmacol. and Taxicol., D. Zakim and D.A. Vessey, Editors, vol. 1: 1–93 (1985).

Dietze, et a; "Spectrophotometric Substrates for Cytosolic Epoxide Hydrolase1"; Analy, Biochem., 216: 176–187 (1994).

Argiriadi, et al; "Detoxification of environmental mutagens and carcinogens: Structure, mechanism, and evolution of liver epoxide hydrolase"; Proc. Natl. Acad. Sci. USA, vol. 96, 1999, 10637–10642.

Yamada, et al; Biochemical Evidence for the Involvement of Tyrosine in Epoxide Activation during the Catalytic Cycle of Epoxide Hydrolase*; J. Biol. Chem. vol. 275, No. 30, 2000, 23082–23088.

Sandberg, et al; "Identification and Functional Characterization of Human Soluble Epoxide Hydrolase Genetic Polymorphisms*"; J. biol. chem., vol. 275, No. 37. 2000, 288873–28881.

Fang, et al; "Pathways of Epoxyeicosatrienoic Acid Metabolism in Endothelial Cells: Implications for the Vascular Effects of Soluble Epoxide Hydrolase Inhibition*"; JBC Papers in Press. Manu. M011761200, Feb. 7, 2001.

Greene, et al; "Toxicity of Epoxy Fatty Acids and Related Compounds to Cells Expressing Human Soluble Hydrolase"; Chem. Res. in Toxicology, vol. 13, No. 4, 2000, 217–226.

Abstract: Dietze, et al; "Inhibition of epoxide hydrolase from human, monkey, bovine, rabbit and murine liver by trans–3–phenylglycidols"; Comp. Biochem. Physiol. B 1993; 104 (2): 309–14.

Abstract: Dietze, et al; "Inhibition of human and murine cytosolic epoxide hydrolase by group–selective reagents."; Comp. Biochem. Physiol. B 1993; 104(2): 299–308.

Abstract: Dietze, et al; "The interaction of cytosolic epoxide hydrolase with chiral epoxides,"; Int. J. Biochem. 1993; 25(1): 43–52.

Abstract: Dietze, et al; "Inhibition on cytosolic epoxide hydrolase by trans–3–phenylglycidols."; Biochem. Pharmacol. 1991; 42(6): 1163–75.

Abstract: Harlarnkar, et al; "Catabolism of epoxy fatty esters by the purified epoxide hydrolase from mouse and human liver."; Arch. Biochem. Biophys. 1989; 272(5): 226–36.

Abstract: Wixtrom, et al; "Continuous spectrophotometric assays for cytosolic epoxide hydrolase,"; Anal. Biochem. 1988; 174(1):291–9.

Abstract: Magdalou, et al; "1,2–Epoxycycloalkanes: substrates and inhibitors of microsomal and cytosolic epoxide hydrolases in mouse liver."; Biochem. Pharmacol. 1988; 37(14):2717–22.

Abstract: Draper, et al; "Identification of CYP2C9 as a human liver microsomal linoleic acid epoxygenase."; Arch. Biochem. Biophys 2000: 376(1):199–205.

Abstract: Mullen, et al; "Differential subcellular localization of endogenous and transfected soluble epoxide hydrolase in mammalian cells: evidence for isozyme.variants.": FEBS Lett 1999: 445(2–3):301–5.

Abstract: Morisseau, et al; "Mechanism of mammalian soluble epoxide hydrolase inhibition by chalcone oxide derivatives."; Arch. Biochem. Biophys. 1998: 356(2):214–28.

Abstract: Moghaddam, et al; "Bioactivation of leukotoxins to their toxic diols by epoxide hydrolase."; Nat. Med. 1997; 3(5):562–6.

Abstract: Borhan, et al; "Improved radiolabeled substrates for solubel epoxide hydrolase."; Anal. Biochem. 1995: 231(1):188–200.

Abstract: Dietze, et al; "Spectropotometric substrates for cytosolic epoxide hydrolase."; Anal. Biochem. 1994; 216(1);176–87.

Abstract: Grant, et al; "Molecular cloning and expression of murine liver soluble epoxide hydrolase."; J. Biol. Chem. 1993; 268(23):17628–33.

Abstract: Beetham, et al; "cDNA cloning and expression of a soluble epoxide hydrolase from human liver."; Arch. Biochem. Biophys. 1993; 305(1):197–201.

Abstract: Greene, et al; "Metabolism of monoepoxides of methyl linoleate: bioactivation and detoxification,"; Arch. Biochem. Biophys 2000; 376(2):420–32.

Abstract: Liao, et al; "Anti–Inflammatory Actions of Cytochrome P450 Epoxygenase–Derived Eicosanoids"; WO 01 01438.

Ingraham, R. H., et al; "Method Of Using Soluble Epoxide hydrolase Inhibitors", U.S. patent application Publication No. 2003/0022929 A1; Jan. 30, 2003.

* cited by examiner

FLUORESCENCE POLARIZATION ASSAY

This application claims the benefit of U.S. Provisional Application No. 60/282,575, filed on Apr. 9, 2001, which is herein incorporated by reference in its entirety.

FIELD OF THE INVENTION

This invention relates generally to a fluorescence polarization assay useful in the detection and evaluation of soluble epoxide hydrolase (sEH) inhibitors. This invention also relates to novel fluorescent probes used in the fluorescence polarization assay, and methods of manufacturing such fluorescent probes.

BACKGROUND OF THE INVENTION

Epoxide hydrolases are a group of enzymes ubiquitous in nature, detected in species ranging from plants to mammals. These enzymes are functionally related in that they all catalyze the addition of water to an epoxide, resulting in a diol. Epoxide hydrolases are important metabolizing enzymes in living systems. Epoxides are reactive species and once formed are capable of undergoing nucleophilic addition. Epoxides are frequently found as intermediates in the metabolic pathway of xenobiotics. Thus in the process of metabolism of xenobiotics, reactive species are formed which are capable of undergoing addition to biological nucleophiles. Epoxide hydrolases are therefore important enzymes for the detoxification of epoxides by conversion to their corresponding, non-reactive diols.

In mammals, several types of epoxide hydrolases have been characterized including soluble epoxide hydrolase (sEH), also referred to as cytosolic epoxide hydrolase, cholesterol epoxide hydrolase, $LTA_4$ hydrolase, hepoxilin hydrolase, and microsomal epoxide hydrolase (Fretland and Omiecinski, Chemico-Biological Interactions, 129: 41–59 (2000)). Epoxide hydrolases have been found in all tissues examined in vertebrates including heart, kidney and liver (Vogel, et al., Eur J. Biochemistry, 126: 425–431 (1982); Schladt et al., Biochem. Pharmacol., 35: 3309–3316 (1986)). Epoxide hydrolases have also been detected in human blood components including lymphocytes (e.g. T-lymphocytes), monocytes, erythrocytes, platelets and plasma. In the blood, most of the sEH detected was present in lymphocytes (Seidegard et al., Cancer Research, 44: 3654–3660 (1984)).

The epoxide hydrolases differ in their specificity towards epoxide substrates. For example, sEH is selective for aliphatic epoxides such as epoxide fatty acids while microsomal epoxide hydrolase (mEH) is more selective for cyclic and arene oxides. The primary known physiological substrates of sEH are four regioisomeric cis epoxides of arachidonic acid known as epoxyeicosatrienoic acids or EETs. These are 5,6-, 8,9-, 11,12-, and 14,15-epoxyeicosatrienoic acid. Also known to be substrates are epoxides of linoleic acid known as leukotoxin or isoleukotoxin. Both the EETs and the leukotoxins are generated by members of the cytochrome P450 monooxygenase family (Capdevila, et al., J. Lipid Res., 41: 163–181 (2000)).

The various EETs appear to function as chemical mediators that may act in both autocrine and paracrine roles. EETs appear to be able to function as endothelial derived hyperpolarizing factor (EDHF) due to their ability to cause hyperpolarization of the membranes of vascular smooth muscle cells with resultant vasodilation (Weintraub, et al., Circ. Res., 81: 258–267 (1997)). EDHF is synthesized from arachidonic acid by various cytochrome P450 enzymes in endothelial cells proximal to vascular smooth muscle (Quilley, et al., Brit. Pharm., 54: 1059 (1997)); Quilley and McGiff, TIPS, 21: 121–124 (2000)); Fleming and Busse, Nephrol. Dial. Transplant, 13: 2721–2723 (1998)). In the vascular smooth muscle cells EETs provoke signaling pathways involving ADP ribosylation of various protein substrates, leading to activation of $BK_{Ca2+}$ (big $Ca^{2+}$ activated potassium channels). This results in hyperpolarization of membrane potential, inhibition of $Ca^{2+}$ influx and relaxation (Li et al., Circ. Res., 85: 349–356 (1999)). Endothelium dependent vasodilation has been shown to be impaired in different forms of experimental hypertension as well as in human hypertension (Lind, et al., Blood Pressure, 9: 4–15 (2000)). Hence, it is likely that enhancement of EETs concentration would have a beneficial therapeutic effect in hypertensive patients where this plays a causative role. Examples of other conditions where enhanced vasodilation could play a positive role include angina, diabetes, stroke, ischemia, and pulmonary hypertension.

Other effects of EETs that may influence hypertension involve effects on kidney function. Levels of various EETs and their hydrolysis products, the DHETs, increase significantly both in the kidneys of spontaneously hypertensive rats (SHR) (Yu, et al., Circ. Res. 87: 992–998 (2000)) and in women suffering from pregnancy induced hypertension (Catella, et al., Proc. Natl. Acad. Sci. U.S.A., 87: 5893–5897 (1990)). In the rat model, both cytochrome P450 and sEH activities were found to increase (Yu et al., Molecular Pharmacology, 2000, 57, 1011–1020). Addition of a known sEH inhibitor was shown to decrease the blood pressure to normal levels. Finally, male soluble epoxide hydrolase null mice exhibited a phenotype characterized by lower blood pressure than their wild-type counterparts (Sinal, et al., J. Biol. Chem., 275: 40504–40510 (2000)).

An analogous effect on smooth muscle appears to operate in the lungs involving epithelial cells and airway smooth muscle relaxation (Dumoulin, et al., Am. J. Physiol., 275 (Lung Cell. Mol. Physiol. 19): L423–L431 (1998); Kiss, et al., Am. J. Resp. Crit. Care Med., 161: 1917–1923 (2000)). Hence, disease states where airways are overly constricted such as asthma, COPD, and bronchitis could benefit from enhanced EETs levels.

EETs, especially 11,12-EET, also have been shown to exhibit anti-inflammatory properties (Node, et al., Science, 285: 1276–1279 (1999); Campbell, TIPS, 21: 125–127 (2000); Zeldin and Liao, TIPS, 21: 127–128 (2000)). Node, et al. have demonstrated 11, 12-EET decreases expression of cytokine induced endothelial cell adhesion molecules, especially VCAM-1. They further showed that EETs prevent leukocyte adhesion to the vascular wall and that the mechanism responsible involves inhibition of NF-KB and IKB kinase.

In addition to the physiological effect of some substrates of sEH (EETs, mentioned above), some diols, i.e. DHETs, produced by sEH may have potent biological effects. For example, sEH metabolism of epoxides produced from linoleic acid (leukotoxin and isoleukotoxin) produces leukotoxin and isoleukotoxin diols (Greene, et al., Arch. Biochem. Biophys. 376(2): 420–432 (2000)). These diols were shown to be toxic to cultured rat alveolar epithelial cells, increasing intracellular calcium levels, increasing intercellular junction permeability and promoting loss of epithelial integrity (Moghaddam et al., Nature Medicine, 3: 562–566 (1997)). Therefore these diols could contribute to the etiology of diseases such as adult respiratory distress syndrome where lung leukotoxin levels have been shown to be elevated (Ishizaki, et al., Pulm. Pharm. & Therap., 12:

145–155 (1999)). Hammock, et al. have disclosed the treatment of inflammatory diseases, in particular adult respiratory distress syndrome and other acute inflammatory conditions mediated by lipid metabolites, by the administration of inhibitors of epoxide hydrolase (WO 98/06261; U.S. Pat. No. 5,955,496).

A number of classes of sEH inhibitors have been identified. Among these are chalcone oxide derivatives (Miyamoto, et al. Arch. Biochem. Biophys., 254: 203–213 (1987)) and various trans-3-phenylglycidols (Dietze, et al., Biochem. Pharm. 42: 1163–1175 (1991); Dietze, et al., Comp. Biochem. Physiol. B, 104: 309–314 (1993)).

More recently, Hammock et al. have disclosed certain biologically stable inhibitors of sEH for the treatment of inflammatory diseases, for use in affinity separations of epoxide hydrolases and in agricultural applications (U.S. Pat. No. 6,150,415). The Hammock '415 patent also generally describes that the disclosed pharmacophores can be used to deliver a reactive functionality to the catalytic site, e.g., alkylating agents or Michael acceptors, and that these reactive functionalities can be used to deliver fluorescent or affinity labels to the enzyme active site for enzyme detection (col. 4, line 66 to col. 5, line 5). Certain urea and carbamate inhibitors of sEH have also been described in the literature (Morisseau et al., *Proc. Natl. Acad. Sci.*, 96: 8849–8854 (1999); Argiriadi et al., *J. Biol. Chem.*, 275 (20) 15265–15270 (2000); Nakagawa et al. *Bioorg. Med. Chem.*, 8: 2663–2673 (2000)).

As outlined in the discussion above, inhibitors of sEH could be useful in the treatment of diseases either by preventing the degradation of sEH substrates that have beneficial effects or by preventing the formation of metabolites that have adverse effects. Therefore, in vitro screens to discover compounds that inhibit sEH are desirable as tools for discovering such inhibitors. Enzymatic assays for sEH activity and for inhibitors of sEH have been reported in the literature and include, for example, a cytosolic sEH enzyme EET assay, a recombinant sEH enzyme EET assay, and a cellular sEH enzyme trans-diphenylpropene oxide (tDPPO) assay. Tests for inhibitors involve adding test compound to a solution of sEH, incubating for a period of time, adding substrate, incubating, and monitoring the formation of diol.

Early sEH assays required preparation and use of a tritium-labeled substrate, a partitioning step and radiometric analysis (S. Gill et al., Analyt. Biochem., 131: 273–282 (1983)). Development of chromatographic assays, for example using HPLC analysis, avoided the use of radiolabeled substrate (R. N. Wixtrom and B. D. Hammock, in Biochemical Pharmacol. and Toxicol., D. Zakim and D. A. Vessey, Editors, Vol. 1: 1–93 (1985)). Each of these assays are time consuming and not amenable to high throughput. Also, in assays which have a partitioning step, followed by analysis of substrate and metabolite (either radiometric or chromatographic), varying extraction efficiencies can make accurate quantitation of substrate and metabolite and discrimination between inhibitors of similar potency difficult.

An improved spectrophotometric assay was described (Dietz et al., Analy. Biochem., 216: 176–187 (1994)), that used s-NEPC (4-nitrophenyl (2S,3S)-2,3-epoxy-3-phenylpropyl carbonate) as a substrate. Enzymatic hydrolysis of the s-NEPC quantitatively releases 4-nitrophenol which is subsequently monitored spectrophotometrically at 405 nm. This method has a very low signal to noise ratio due to the fact that 4-nitrophenol does not have a strong absorbance signal. In addition, s-NEPC is subject to auto hydrolysis. Both these factors make data analysis challenging. Although this assay is amenable to a 96-well plate format, the low signal to noise ratio makes this assay unfeasible for an ultra-high throughput screening approach.

In contrast to these known assays, the sEH fluorescence polarization assay of the present invention is a very sensitive and highly reproducible assay. This facilitates the determination of structure-activity relationships and the ranking of closely related test sEH inhibitors. It also has a very high signal to noise ratio, is not subject to auto hydrolysis since it is not an enzyme assay and is amenable to high throughput screening.

SUMMARY OF THE INVENTION

The present invention is directed to a fluorescence polarization assay for the detection and evaluation of sEH inhibitors that overcomes the aforementioned disadvantages of known assays.

A key feature of the fluorescence polarization assay of the present invention is the use of a novel fluorescent probe that binds to the active site of soluble epoxide hydrolase. This fluorescent probe, which constitutes another aspect of the present invention, is a compound having the following formula (I):

X-spacer-$R_1$-Y     (I)

wherein X is the radical of compound that binds to the active site of soluble epoxide hydrolase, Y is a fluorescent label, "spacer" is a direct bond or is a $C_1$–$C_{16}$ alkylene group, a $C_2$–$C_{16}$ alkenylene group or a $C_2$–$C_{16}$ alkynylene group, wherein any of the available —$CH_2$— groups present in the $C_1$–$C_{16}$ alkylene group, $C_2$–$C_{16}$ alkenylene group or $C_2$–$C_{16}$ alkynylene group can optionally be replaced with O, S(O)$_p$ wherein p is 0 to 2, or N($R_2$), $R_1$ is selected from the group consisting of O, S, —N($R_2$)C(O)—, —C(O)N($R_2$)—, —N($R_2$)C(S)—, —C(S)N($R_2$)—, —N($R_2$)C(S)NH—, —NHC(S)N($R_2$), —N($R_2$)C(O)NH—, —NHC(O)N($R_2$), —SO$_2$N$R_2$—, —NR$_2$SO$_2$—, —CH$_2$N($R_2$)—, —N($R_2$)CH$_2$—, —CH$_2$S—, —SCH$_2$—, —C(O)CH$_2$S—, —SC(O)CH$_2$—, —NHCH$_2$CH$_2$S—, —SCH$_2$CH$_2$NH—, —NC(O)O—, —ONC(O)—, —C(O)O—, —OC(O)—, —NH—N=C($R_2$)—, —C($R_2$)=N—NH—, —NHCH($R_2$)—, or —CH($R_2$)NH—, and $R_2$ is selected from H or $C_{1-3}$alkyl.

The fluorescence polarization assay of the present invention generally comprises the following steps:

(a) determining the fluorescence polarization values of the free fluorescent probe and the fluorescent probe bound to soluble epoxide hydrolase to obtain a range of fluorescence polarization values and selecting a reference fluorescence polarization value falling within that range;

(b) mixing the fluorescent probe with soluble epoxide hydrolase in a buffered aqueous solution;

(c) mixing a test compound with the mixture obtained in step (b) and incubating the resulting mixture of fluorescent probe, soluble epoxide hydrolase and test compound;

(d) measuring the fluorescence polarization value of the incubated mixture obtained in step (c) to obtain a test fluorescence polarization value; and (e) determining the difference between the test fluorescence polarization value and the reference fluorescence polarization value;

wherein the difference in fluorescence polarization values obtained in step (e) indicates whether the test compound inhibits soluble epoxide hydrolase.

The assay of the present invention is very sensitive and highly reproducible and can detect compounds that positively or negatively affect probe binding to the active site of soluble epoxide hydrolase by analyzing corresponding changes in fluorescence polarization, e.g., both competitive and allosteric inhibitors of sEH can be easily detected and evaluated. This assay is useful with respect to a variety of soluble epoxide hydrolases from different species and can also be used in high throughput screening procedures, e.g., efficiently screening a library of test compounds for soluble epoxide hydrolase inhibitory activity.

DETAILED DESCRIPTION OF THE INVENTION

I. The Fluorescent Probes

The fluorescent probes of the present invention bind to the active site of soluble epoxide hydrolase and have the following general formula (I):

X-spacer-$R_1$-Y     (I)

wherein X is the radical of compound that binds to the active site of soluble epoxide hydrolase, Y is a fluorescent label, "spacer" is a direct bond or is a $C_1$–$C_{16}$ alkylene group, a $C_2$–$C_{16}$ alkenylene group or a $C_2$–$C_{16}$ alkynylene group, wherein any of the available —$CH_2$— groups present in the $C_1$–$C_{16}$ alkylene group, $C_2$–$C_{16}$ alkenylene group or $C_2$–$C_{16}$ alkynylene group can optionally be replaced with O, $S(O)_p$ wherein p is 0 to 2, or $N(R_2)$, $R_1$ is selected from the group consisting of O, S, —$N(R_2)C(O)$—, —$C(O)N(R_2)$—, —$N(R_2)C(S)$—, —$C(S)N(R_2)$—, —$N(R_2)C(S)NH$—, —$NHC(S)N(R_2)$, —$N(R_2)C(O)NH$—, —$NHC(O)N(R_2)$, —$SO_2NR_2$—, —$NR_2SO_2$—, —$CH_2N(R_2)$—, —$N(R_2)CH_2$—, —$CH_2S$—, —$SCH_2$—, —$C(O)CH_2S$—, —$SC(O)CH_2$—,

—$NHCH_2CH_2S$—, —$SCH_2CH_2NH$—, —$NC(O)O$—, —$ONC(O)$—, —$C(O)O$—, —$OC(O)$—, —$NH$—$N$=$C(R_2)$—, —$C(R_2)$=$N$—$NH$—, —$NHCH(R_2)$—, or —$CH(R_2)NH$—, and $R_2$ is selected from H or $C_{1-3}$alkyl.

The assay of the present invention is expected to be useful to detect inhibitors of soluble epoxide hydrolases from various species in view of the structural similarities of the sEH molecules from different organisms. Accordingly, moiety X in the fluorescent probe of the present invention would be selected such that it binds to the active site of the specific soluble epoxide hydrolase under investigation, such that inhibitors of that specific soluble epoxide hydrolase could be detected by the assay. For example, X can be the radical of a compound that binds to the active site of a mammalian soluble epoxide hydrolase, for example, human soluble epoxide hydrolase or murine soluble epoxide hydrolase, in order to detect inhibitors of these specific hydrolases.

Compounds that bind to the active site of soluble epoxide hydrolase include any of the sEH inhibitors well known in the art. See, e.g., WO 98/06261; U.S. Pat. No. 5,955,496; U.S. Pat. No. 6,150,415; WO 00/23060; Miyamoto, et al., Arch. Biochem. Biophys., 254: 203–213 (1987); Dietze, et al., Biochem. Pharm., 42: 1163–1175 (1991); Morisseau et al., Proc. Natl. Acad. Sci., 96: 8849–8854 (1999); Argiriadi et al., J. Biol. Chem., 275 (20): 15265–15270 (2000); and Nakagawa et al. Bioorg. Med. Chem., 8: 2663–2673 (2000). Additional sEH inhibitors include those disclosed in U.S. Provisional Application No. 60/302,066 (Ingraham et al.), filed Jun. 29, 2001. The X moiety of the present invention can thus be derived from such sEH inhibitory compounds, modified as necessary to include any appropriate chemical functionality for linking to the spacer or $R_1$ group in the compounds of the formula (I) above, as would be understood by one skilled in the art.

It has recently been demonstrated that the sEH gene locus exhibits genetic polymorphism (Sandberg, et al., J. Biol. Chem., 275: 28873–28881 (2000)). It is also possible that splice variants or isoforms or differentially processed forms of the native enzyme may exist. The term "soluble epoxide hydrolase" as used herein is intended to include all such varieties of soluble epoxide hydrolase.

Preferred fluorescent probes of the present invention are those having the following formula (II):

wherein:
$R_1$, Y and "spacer" are as defined above;
D is selected from $N(R_4)$, O or S;
E is selected from C(=Z), P(=Z) or S;
F is selected from $N(R_5)$, O, S, $CH_2$ or $N(R_5)C(O)$;
G is a direct bond or is $C_{1-6}$alkylene;
Z is O, S or $N(R_7)$;
$R_3$ is $C_{1-20}$alkyl, $C_{2-20}$ alkenyl, $C_{2-20}$ alkynyl, $C_{3-10}$ cycloalkyl, $C_{5-7}$cycloalkenyl, $C_{1-6}$acyl, aryl, aryl-$C_{1-6}$alkyl, heteroaryl or heterocycle, each being optionally substituted with one or more $C_{1-3}$alkyl, halogen, CN, OH, $NH_2$, $C_{1-3}$alkyloxy, $C_{1-3}$alkylthio, $C_{1-3}$acyloxy, $C_{1-3}$acylthio, $C_{1-3}$alkylamino, $C_{1-3}$dialkylamino, $C_{1-3}$acylamino, $C_{1-3}$diacylamino or $C_{1-3}$alkyl($C_{1-3}$acyl)amino,
$R_4$ and $R_5$ are independently selected from H or $C_{1-6}$alkyl, but at least one of $R_4$ and $R_5$ is hydrogen;
$R_6$ is selected from $C_{1-20}$alkylene, $C_{2-20}$ alkenylene, $C_{2-20}$ alkynylene, $C_{3-10}$ cycloalkylene, $C_{5-7}$cycloalkenylene, $C_{1-6}$acyl, aryl, heteroaryl, heterocycle or a $C_{6-12}$ bridged carbocyclic ring system, optionally having one to three double bonds in the ring system, each being optionally substituted with one or more $C_{1-3}$alkyl, halogen, CN, OH, $NH_2$, $C_{1-3}$alkyloxy, $C_{1-3}$alkylthio, $C_{1-3}$acyloxy, $C_{1-3}$acylthio, $C_{1-3}$alkylamino, $C_{1-3}$dialkylamino, $C_{1-3}$acylamino, $C_{1-3}$diacylamino, $C_{1-3}$alkyl($C_{1-3}$acyl)amino or aryloxy; and $R_7$ is selected from H or $C_{1-6}$alkyl.

More preferred fluorescent probes are those having the following formula (III):

(III)

wherein:

Z is O or S; and $R_1$, $R_3$, $R_4$, $R_6$, F, G, "spacer" and Y are as defined immediately above.

A preferred subgenus of fluorescent probes include those having the formula (III) above and wherein:

F is selected from N($R_5$) and O;

G is a direct bond or is $C_{1-3}$alkylene;

Z is O;

"spacer" is a $C_{1-6}$alkylene group;

$R_1$ is —N($R_2$)C(O)—, —C(O)N($R_2$)—, —N($R_2$)C(S)— or —C(S)N($R_2$)—, where $R_2$ is H or $C_{1-3}$alkyl;

$R_3$ is $C_{1-6}$alkyl, $C_{2-6}$ alkenyl, $C_{2-6}$ alkynyl, $C_{5-7}$ cycloalkyl, or phenyl, each being optionally substituted with one or more $C_{1-3}$alkyl, halogen, CN, $C_{1-3}$alkoxy or $C_{1-3}$alkylthio;

$R_4$ and $R_5$ are both hydrogen; and

$R_6$ is selected from $C_{1-6}$alkylene, $C_{2-6}$ alkenylene, $C_{2-6}$ alkynylene, $C_{5-7}$cycloalkylene, phenyl or a $C_{6-12}$ bridged carbocyclic ring system, optionally having one to three double bonds in the ring system, each being optionally substituted with one or more $C_{1-3}$alkyl, halogen, CN, $C_{1-3}$alkoxy or $C_{1-3}$alkylthio.

Fluorescent labels suitable for use in the invention include any of those well known in the art. See, for example, those described in "Handbook of Fluorescent Probes and Research Chemicals" by Richard P. Haugland, Sixth edition (1996). The seventh edition is available on CD-ROM and an updated seventh edition is available on the Web at www.probes.com/handbook/. A number of suitable fluorescent labels are commercially available from Molecular Probes, Inc. It is preferred that the fluorescent label fluoresces at a relatively high wavelength, i.e., above about 450 nm, to avoid interference from cell originating fluorescence and fluorescence originating from test compounds and impurities present in the system or from glass and plastic containers. Accordingly, in one embodiment, the fluorescent label of the invention fluoresces at a wavelength above about 450 nm. More preferably, the label fluoresces above about 550 nm, and less than about 700 nm.

Examples of fluorescent labels useful in the present invention include rhodamine and rhodamine derivatives such as tetramethyl rhodamine, carboxytetramethylrhodamine, Lissamine™ Rhodamine B, Texas Red®, carboxy-X-rhodamine and Rhodamine Red™-X, and other rhodamine derivatives known in the art, fluorescein and fluorescein derivatives such as fluorinated fluoresceins such as Oregon Green® and its derivatives, fluoresceinamine, carboxyfluorescein, alpha-iodoacetamidofluorescein, 4'-aminomethylfluorescein, 4'-N-alkylaminomethylfluorescein, 5-aminomethylfluorescein, 6-aminomethylfluorescein, 2,4-dichloro-1,3,5-triazin-2-yl-aminofluorescein (DTAF), 4-chloro-6-methoxy-1,3,5-triazin-2-yl-aminofluorescein, and fluoresceinisothiocyanate, and other fluorescein derivatives known in the art, 4,4-difluor-4-bora-3a,4a-diaza-s-indacene and its derivatives, cyanine dyes, and the Alexa Fluor® dyes.

More preferred fluorescent labels include rhodamine, tetramethyl rhodamine, carboxytetramethylrhodamine, Lissamine™ Rhodamine B, Texas Red®, carboxy-X-rhodamine, Rhodamine Red™-X, Oregon Green® dyes 488, 500, and 514, BODIPY® derivatives, Cy3™, Cy5™, and the Alexa Fluor® dyes 488, 532, 546, 568, 594, 633, 660 and 680.

The following is a specific example of a fluorescent probe falling within the scope of the present invention:

Any fluorescent probes of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes all such tautomers.

The compounds of the invention are only those which are contemplated to be 'chemically stable' as will be appreciated by those skilled in the art. For example, compounds which would have a 'dangling valency', or a 'carbanion' are not compounds contemplated by the invention.

All terms as used herein in this specification, unless otherwise stated, shall be understood in their ordinary meaning as known in the art. All alkyl, alkylene, alkenyl, alkenylene, alkynyl and alkynylene groups shall be understood as being branched or unbranched unless otherwise specified. Other more specific definitions are as follows:

The term "acyl", when used alone or in combination with another group, shall be understood to mean an R—(C=O)— moiety wherein R is an alkyl group. Examples of R can be a $C_{1-10}$alkyl, saturated or unsaturated, branched or unbranched. The term "acyloxy" shall be understood to mean an R—$CO_2$— group wherein R is as defined in this paragraph. Likewise, "acylthio" shall be understood to mean an R—C(O)—S— group wherein R is as defined in this paragraph.

The term "alkylene" shall be understood to mean a saturated, divalent hydrocarbon chain, i.e., generally present as a bridging group between two other groups. Examples of alkylene groups include —$CH_2$— (methylene); —$CH_2CH_2$— (ethylene); —$CH_2CH_2CH_2$— (propylene), etc. The term "alkenylene" shall be understood to mean a divalent hydrocarbon chain having one or more double bonds within the chain, i.e., generally present as a bridging group between two other groups. Examples of alkenylene groups include —CH=CH— (ethenylene); —CH=CHCH$_2$— (1-propenylene), —CH=CHCH$_2$CH$_2$— (1-butenylene), —CH$_2$CH=CHCH$_2$— (2-butenylene), etc.

The term "alkynylene" shall be understood to mean a divalent hydrocarbon chain having one or more triple bonds within the chain, i.e., generally present as a bridging group between two other groups. Examples of alkenylene groups include —C≢C—; —C≢CCH$_2$—; —C≢CCH$_2$CH$_2$—; —CH$_2$C≢CCH$_2$—, etc.

The term "aryl" shall be understood to mean a 6–10 membered aromatic carbocycle; "aryl" includes, for example, phenyl and naphthyl; other terms comprising "aryl" will have the same definition for the aryl component, examples of these moieties include: arylalkyl, aryloxy or arylthio.

The term "cycloalkenyl" shall be understood to mean a cycloalkyl group wherein one or more of the single bonds in the cycloalkyl ring are replaced by double bonds.

The terms "cycloalkylene" and "cycloalkenylene" shall be understood to mean divalent cycloalkyl and cycloalkenyl groups, respectively, i.e., generally present as bridging groups between two other groups.

The term "halogen" as used in the present specification shall be understood to mean bromine, chlorine, fluorine or iodine.

The term "heteroaryl" refers to a stable 5–8 membered (but preferably, 5 or 6 membered) monocyclic or 8–11 membered bicyclic aromatic heterocycle radical. Each heterocycle consists of carbon atoms and from 1 to 4 heteroatoms chosen from nitrogen, oxygen and sulfur. The heterocycle may be attached by any atom of the cycle, which results in the creation of a stable structure. Example "heteroaryl" radicals include, pyridyl, pyrimidinyl, pyrazinyl, pyridazinyl, pyrrolyl, imidazolyl, pyrazolyl, thienyl, furyl, isoxazolyl, isothiazolyl, oxazolyl, thiazolyl, oxadiazolyl, thiadiazolyl, quinolinyl, isoquinolinyl, indolyl, benzimidazolyl, benzofuranyl, benzoxazolyl, benzisoxazolyl, benzpyrazolyl, benzothiofuranyl, benzothiazolyl, quinazolinyl and indazolyl, or a fused heteroaryl such as cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene;

The term "heterocycle" refers to a stable 5–8 membered (but preferably, 5 or 6 membered) monocyclic or 8–11 membered bicyclic heterocycle radical which may be either saturated or unsaturated, and is non-aromatic. Each heterocycle consists of carbon atoms and from 1 to 4 heteroatoms chosen from nitrogen, oxygen and sulfur. The heterocycle may be attached to the main structure by any atom of the cycle, which results in the creation of a stable structure. Example "heterocycle" radicals include pyrrolinyl, pyrrolidinyl, pyrazolinyl, pyrazolidinyl, 1,2,5,6-tetrahydropyridinyl, piperidinyl, morpholinyl, thiomorpholinyl, pyranyl, thiopyranyl, piperazinyl, indolinyl, and 1,2,3,3a,4,6a-hexahydro-cyclopenta[c]pyrrolyl.

As used herein and throughout this specification, the terms "nitrogen" and "sulfur" and their respective elements symbols include any oxidized form of nitrogen and sulfur and the quaternized form of any basic nitrogen.

The "$C_{6-12}$ bridged carbocyclic ring system, optionally having one to three double bonds in the ring system" shall be understood to mean any carbocyclic ring system containing 6 to 12 carbon atoms and having at least one bridged-type fusion within the ring system. An example is a $C_{6-10}$carbocyclic ring system, optionally having one or two double bonds in the system. Examples of such a ring system are bicyclo[2.2.1]heptane and adamantane.

General Synthetic Methods

The fluorescent probes of the invention may be prepared by the methods described below. In each of the methods and schemes described below, the groups X, spacer, Y, $R_1$ through $R_7$, D, E, F, G and Z, where shown, are as defined above for general formulas I, II and III except as noted. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Typically, reaction progress may be monitored by thin layer chromatography (TLC) if desired. Intermediates and products may be purified by chromatography on silica gel and/or recrystallization. Starting materials and reagents are either commercially available or may be prepared by one skilled in the art using methods described in the chemical literature.

As discussed above, the X moiety of formula (I) can correspond to any of the soluble epoxide hydrolase inhibitor compounds known in the art. Depending on the D, E and F groups selected in formula (II) shown above, the X moiety of formula (I) can contain various functional groups that are present in the various sEH inhibitors known in the art and cited above. These functional groups include ureas ($R_3N(R_4)$—C(O)—N($R_5$)—), thioureas ($R_3N(R_4)$—C(S)—N($R_5$)—), carbamates ($R_3OC(O)$—N($R_5$)—) or ($R_3N(R_4)$—C(O)—O—), amides ($R_3N(R_4)$—C(O)—$CH_2$—) etc. The synthesis of these various compounds corresponding to moiety X may be accomplished by methods known to those skilled in the art. Particular intermediates chosen for these syntheses will depend on the particular D, E and F selected.

For example, compounds of formula (II) wherein $R_1$ is —N($R_2$)C(O)—, D is —N($R_4$)—, E is C(=Z)— and F is N($R_5$) may be synthesized as illustrated in Scheme 1 below:

A fluorescent label Y containing a carboxylic acid group, compound IV, is reacted with a diamine compound of formula V under standard coupling conditions. Suitable coupling conditions include making an active ester of compound IV, for example, a hydroxysuccinimide ester, and reacting this ester with the compound of formula V in an suitable inert solvent, such as dimethylformamide (DMF) or tetrahydrofuran (THF), to prepare an amino carboxamide compound of formula VI. Alternatively, one may react IV with V in the presence of a coupling reagent known in the art, such as a carbodiimide reagent. Depending on the nature of $R_2$ and $R_5$, protection and deprotection strategies known in the art may be employed to optimize the formation of the desired amide functionality $NR_2C(O)Y$ in formula VI.

In one embodiment, the compound of formula VI is then reacted with an isocyanate or isothiocyanate ($R_3N=C=Z$, wherein Z=O or S) in the presence of a suitable base, such as a trialkylamine, in a suitable inert solvent, such as DMF or THF, to give the fluorescent probe of formula IIa (providing compounds of formula II wherein $R_4$ is H). In another embodiment, the compound of formula VI is then reacted with a carbamoyl chloride or thiocarbamoyl chloride ($R_3R_4N(C=Z)Cl$ wherein $R_4$ is $C_{1-6}$alkyl, Z=O or S) in the presence of a suitable base, such as a trialkylamine, in a suitable inert solvent, such as DMF or THF, to give the fluorescent probe of formula IIb (providing compounds of formula II wherein $R_4$ is $C_{1-6}$alkyl). The methods described above to obtain the compounds of formula IIa and IIb from the compound of formula VI can be employed to produce urea- and thiourea-containing X moieties, i.e., where D—E—F is $N(R_4)C(=Z)N(R_5)$ in formula (II).

The synthesis of other types of X moieties may be accomplished by methods known to those skilled in the art. Some illustrative examples of such method are shown in the scheme below using the intermediates shown in Table 1 below.

TABLE 1

| $R_3V + W$-G-$R_6$-spacer- → $R_3$-D-E-F-G-$R_6$-spacer- | | |
|---|---|---|
| $R_3$—V | W-G-$R_6$-spacer- | $R_3$-D-E-F-G-$R_6$-spacer- |
| $R_3$—N=C=O | HO-G-$R_6$-spacer- | $R_3$—NHC(O)O-G-$R_6$-spacer- |
| $R_3$—$NH_2$ | $HO_2CCH_2$-G-$R_6$-spacer- | $R_3$—NHC(O)$CH_2$-G-$R_6$-spacer- |
| $R_3$—OH | O=C=N-G-$R_6$-spacer- | $R_3$—OC(O)NH-G-$R_6$-spacer- |
| $R_3$OH | $HO_2CCH_2$-G-$R_6$-spacer- | $R_3$OC(O)$CH_2$-G-$R_6$-spacer- |

A variety of fluorescent labels suitable as Y are available commercially (see for example Molecular Probes, Inc. at www.probes.com). These labels are available with a variety of reactive functionalities that may be coupled to an appropriately substituted "spacer" group to produce the connecting moiety $R_1$ between the spacer and the fluorescent label group Y in the compounds of formula (I). The connecting moiety $R_1$ obtained will depend on the spacer group and reactive functionality chosen. For example, in the first step of Scheme 1 above, a fluorescent label Y having a $CO_2H$ group, i.e., the compound Y—$CO_2H$, is reacted with a spacer derivative having an amine functionality, i.e., the compound . . . -spacer-$NHR_2$, to obtain a compound of formula (I) wherein $R_1$ is —N($R_2$)C(O)—.

The general scheme and Table 2 below shows examples of other reactive functionalities (Q) on fluorescent probes that are commercially available and the $R_1$ group that may be formed by reaction with functional groups (L) present on substituted spacer groups. Reaction conditions are known to those skilled in the art. Generally they involve combining the fluorescent label containing the reactive functionality (Y—Q) with the desired spacer group (spacer-L) in a suitable solvent, such as methylene chloride, ethyl acetate, THF or DMF, optionally in the presence of an appropriate catalyst, as would be known in the art, for example a base such as triethylamine, or a coupling reagent, at a suitable temperature of about −10° C. to the reflux temperature of the solvent, preferably at about 0° C. to room temperature. Particular reaction conditions and reaction times can vary depending on the nature of Y—Q and spacer-L. Reaction progress is easily monitored by methods known in the art such as thin layer chromatography.

TABLE 2

Y—Q + spacer-L → spacer-$R_1$—Y

| Y–Q | spacer-L | spacer-$R_1$—Y |
|---|---|---|
| Y—N=C=S | spacer-HN($R_2$) | spacer-N$R_2$C(S)N—Y |
| Y—N=C=O[1] | " | spacer-N$R_2$C(O)N—Y |
| Y—SO$_2$Cl | " | spacer-N$R_2$SO$_2$—Y |
| Y—CHO | " | spacer-N($R_2$)CH$_2$—Y[2] |
| Y—CH$_2$—R'(R' = I, Br or Cl) | spacer-SH | spacer-SCH$_2$—Y |
| Y—C(O)CH$_2$R' | " | spacer-SCH$_2$C(O)Y |
| Y-maleimide | " | spacer-S-maleimide-Y |
| Y—N(aziridine) | " | spacer-SCH$_2$CH$_2$NH—Y |
| Y—N=C=O[1] | spacer-OH | spacer-OC(O)NH—Y |
| Y—CO$_2$H | spacer-OH | spacer-OC(O)—Y |
| Y—NHNH$_2$ | spacer-C(O)$R_2$ | spacer-C($R_2$)=N—NH—Y |
| Y—NH$_2$ | spacer-C(O)$R_2$ | spacer-CH($R_2$)NH—Y[2] |
| Y—NH$_2$ | spacer-CO$_2$H | spacer-C(O)NH—Y |

[1]Readily prepared from the commercially available acyl azide by heating in an organic solvent (Curtius rearrangement).
[2]Following reduction of the intermediate imine with a suitable reducing agent such as sodium borohydride.

Using the methods described above, one skilled in the art could readily prepare the various fluorescent probes (I) falling within the scope of the present invention.

II. The Fluorescence Polarization Assay

Fluorescence polarization immunoassay procedures have been used to provide a reliable quantitative means for measuring the amount of tracer-antibody complex produced in a homogeneous competitive binding assay. Typically, in such a competitive binding immunoassay a ligand (a substance of biological interest to be determined by the technique) competes with a fluorescently labeled reagent, or "ligand analog" or "tracer", for a limited number of receptor binding sites on antibodies specific to the ligand and ligand analog. The concentration of ligand in the sample determines the amount of ligand analog which binds to the antibody: the amount of ligand analog that will bind is inversely proportional to the concentration of ligand in the sample, because the ligand and the ligand analog each bind to the antibody in proportion to their respective concentrations.

Fluorescence polarization techniques are based on the principle that a fluorescent labeled compound, when excited by plane polarized light, will emit fluorescence having a degree of polarization inversely related to its rate of rotation. Accordingly, when a tracer-antibody complex having a fluorescent label, for example, is excited with plane polarized light, the emitted light remains highly polarized because the fluorophore is constrained from rotating between the time that light is absorbed and emitted. In contrast, when a "free" tracer compound (i.e., unbound to an antibody) is excited by plane polarized light, its rotation is much faster than that of the corresponding tracer-antibody conjugate and the molecules are more randomly oriented. As a result, the light emitted from the unbound tracer molecules is depolarized.

The present inventors have discovered that the novel fluorescent probes of the present invention can be used in a fluorescence polarization assay to detect and evaluate inhibitors of soluble epoxide hydrolase. The fluorescent probes of the present invention specifically bind to the active site of soluble epoxide hydrolase. Upon complexing with the sEH enzyme, the probe-sEH complex thus formed assumes the rotation of the sEH molecule which is slower than that of the relatively small fluorescent probe molecule, thereby increasing the polarization observed. When an sEH inhibitor test compound competes with the fluorescent probe for the active site of sEH, less probe-sEH complex is formed, i.e., there is more probe in an uncomplexed, free form. Therefore, the observed polarization of fluorescence of the resulting mixture of free probe and probe-sEH complex assumes a value intermediate between that of the free probe and that of the probe-sEH complex. Thus, there is a reduction of the fluorescence polarization value in the presence of a competitive inhibitor of sEH as compared to when no such inhibitor is present. Inhibitor dissociation constants can then be easily determined in order to evaluate the relative strength of the competitive sEH inhibitor.

The fluorescent probes of the invention can also be used to detect and evaluate non-competitive inhibitors of sEH, e.g., allosteric inhibitors, that bind to a site on the soluble epoxide hydrolase molecule other than the active site but affect binding at the active site. The effect of the non-competitive inhibitor on active site binding, either positive or negative, can be detected in the assay by corresponding changes in the fluorescence polarization value, said changes demonstrating either enhancement or suppression of probe binding at the active site.

Unless otherwise specified herein, the conditions that can be employed in running the fluorescence polarization assays of the present invention (e.g., pressure, temperature, pH, solvents, time) may be readily determined by one having ordinary skill in the art. Of course, the optimum assay conditions may vary depending on the particular reagents used (i.e., the fluorescent probe, the soluble epoxide hydrolase and the test compound) and such optimum conditions can also be readily determined by one skilled in the art based on the general knowledge in the field of fluorescence polarization.

In one embodiment, the fluorescence polarization assay of the present invention comprises the following steps:
 (a) determining the fluorescence polarization values of the free fluorescent probe and the fluorescent probe bound to soluble epoxide hydrolase to obtain a range of fluorescence polarization values and selecting a reference fluorescence polarization value falling within that range;
 (b) mixing the fluorescent probe with soluble epoxide hydrolase in a buffered aqueous solution;
 (c) mixing a test compound with the mixture obtained in step (b) and incubating the resulting mixture of fluorescent probe, soluble epoxide hydrolase and test compound,
 (d) measuring the fluorescence polarization value of the incubated mixture obtained in step (c) to obtain a test fluorescence polarization value; and
 (e) determining the difference between the test fluorescence polarization value and the reference fluorescence polarization value;
 wherein the difference in fluorescence polarization values obtained in step (e) indicates whether the test compound inhibits soluble epoxide hydrolase.

As a preliminary step, it is desirable to determine the wavelengths of maximum excitation and emission of the particular fluorescent probe selected to be used in the assay, unless these values are already known. These wavelengths can be determined using any conventional technique, for example, by measuring the respective excitation and emission wavelengths of the probe in a suitable assay buffer using a fluorimeter.

In step (a) of the assay, the affinity of the fluorescent probe for soluble epoxide hydrolase is determined by measuring the fluorescence polarization values of the free (unbound) fluorescent probe and the fluorescent probe bound to soluble epoxide hydrolase to obtain a range of fluorescence polarization values. The polarization value of the free fluorescent probe would usually be the minimum value in this range and, likewise, the polarization value of the bound fluorescent probe would usually be the maximum value in this range. In one embodiment, this range of fluorescence polarization values in step (a) is obtained by periodically adding increasing amounts of soluble epoxide hydrolase to an amount of fluorescent probe in a buffered aqueous solution, for example by titration, and then measuring the fluorescence polarization value of this mixture after each addition of i soluble epoxide hydrolase until no further significant change in polarization value is observed. If desired, one may then use the data obtained in conjunction with conventional methods (e.g., regression analysis) to calculate the dissociation constant of the fluorescent probe for the soluble epoxide hydrolase.

From the results obtained in step (a), one can then select an appropriate reference fluorescence polarization value for use in the assay, this reference fluorescence polarization value falling in the range of polarization values obtained in step (a). One skilled in the art can best determine the particular reference polarization value to use in the assay, depending on the affinity of the specific fluorescent probe for sEH, the expected inhibitory strength of the test compound, and other conditions and variables.

In general, however, the reference fluorescence polarization value is selected such that it falls within the upper half of the range of polarization values obtained in step (a). For example, the reference fluorescence polarization value may be selected such that the difference between the reference fluorescence polarization value and the polarization value of free fluorescent probe is equal to about 50% to 100%, preferably about 80% to 100%, of the difference between the polarization value of fluorescent probe bound to soluble epoxide hydrolase and the polarization value of free fluorescent probe.

In the next step (b), the fluorescent probe is mixed with the soluble epoxide hydrolase in a buffered aqueous solution in order to form a complex between the fluorescent probe and the sEH. The concentrations of the fluorescent probe and the sEH should be chosen so as to facilitate competition between the probe and the test compounds for binding to sEH and will depend on a number of factors including the binding affinity of the probe for sEH. The appropriate concentrations to use in a particular assay can be readily determined by one skilled in the art.

In the next step (c), a test compound is mixed with the fluorescent probe-sEH complex mixture obtained in step (b), and the resulting mixture of fluorescent probe, soluble epoxide hydrolase and test compound is incubated to facilitate competition or other interaction. In one embodiment, the test compound may be dissolved in a buffered aqueous solution prior to mixing it with the probe-sEH mixture. If the test compound is water-insoluble, it may be necessary to first dissolve the test compound in an appropriate organic solvent, for example DMSO, prior to diluting it in the buffered aqueous solution. If an organic solvent is used, the final percent organic solvent in the assay mixture should not exceed about 1%. The incubation conditions for this step can vary, but generally the incubation is conducted at a temperature of about 25 degrees centigrade for about 15 minutes.

The fluorescence polarization value of the incubated mixture is then measured, step (d), in order to obtain a test fluorescence polarization value. The fluorescence polarization can be measured using well known techniques in the art, as described hereinafter. For example, the polarization can be measured using a fluorescence polarization plate reader set at the wavelength appropriate for the fluorescent label on the fluorescent probe. The difference between the test fluorescence polarization value obtained in step (d) and the reference fluorescence polarization value will then indicate whether the test compound is an inhibitor of soluble epoxide hydrolase and the relative strength of the inhibitory effect, if any.

When the difference in fluorescence polarization values obtained in step (d) is positive, i.e., there is an increase in the polarization in the presence of test compound, this could indicate that the test compound is a non-competitive (allosteric) inhibitor of sEH that functions to enhance the binding of the fluorescent probe to the sEH molecule. Where the difference in fluorescence polarization values obtained in step (d) is negative, i.e., there is a decrease in the polarization in the presence of test compound, this could indicate that the test compound is a competitive inhibitor of sEH that competes with the fluorescent probe for active site binding on the sEH molecule.

When the assay is run using multiple dilutions of a test compound, the range of test fluorescence polarization values obtained can be plotted on an appropriate graph. If desired, one may then use conventional methods (e.g., regression analysis) to calculate the dissociation constant of the test compound for binding to soluble epoxide hydrolase.

The assay of the present invention can be run at a wide range of pH levels. In general, the pH may range from about 3 to 12, more usually from about 5 to 10, preferably from about 5 to 8. Various buffers may be used to achieve and maintain the pH during the assay procedure. Representative buffers for use in the assay include borate, phosphate, carbonate, TRIS, TES, and the like. The salt concentration of the buffer may fall within a wide range, but preferably the salt concentration is between 0 and about 600 mM. The buffered aqueous solution preferably further contains a reducing agent such as dithiothreitol and it is preferred that the buffer contains a detergent, such as CHAPS or any other conventional detergent normally used in buffers. Within these parameters the particular buffer employed is not critical to the present invention, but in an individual assay a specific buffer may be preferred in view of the other conditions and reagents employed, as can readily be determined by one skilled in the art.

As discussed above, the fluorescence polarization values can be measured using techniques that are well known in the art. For example, by measuring the vertically and horizontally polarized components of the emitted light, the polarization of fluorescence in the reaction mixture may be accurately determined. (see Chapter 10 in "Principals of Fluorescence Spectroscopy" Second edition, J. R. Lakowizc, Kluwer Academic/Plenum Publishers, New York 1999 for detailed description of measurement).

The assay can be run using soluble epoxide hydrolases from a variety of species, but a mammalian soluble epoxide hydrolase is preferred, for example, human or murine soluble epoxide hydrolase. The various soluble epoxide hydrolases that can be used in assay of the present invention are well known in the art and are described, for example, in the following references: Schladt, et al. Eur. J. Biochem. 176: 31–37 (1988); Schladt, et al. Eur. J. Biochem. 176: 715–723 (1988); Beetham, et al., Arch. Biochem. Biophys. 305: 197–201 (1993); Silva and Hammock, Comp. Biochem. Physiol. 87B: 95–102 (1987).

In another embodiment, the fluorescence polarization assay of the present invention can be employed to quickly and efficiently screen a library of test compounds for sEH inhibitory activity. This assay comprises the following steps:

(a) determining the fluorescence polarization values of the free fluorescent probe and the fluorescent probe bound to soluble epoxide hydrolase to obtain a range of fluorescence polarization values and selecting a reference fluorescence polarization value falling within that range;

(b) mixing the fluorescent probe with soluble epoxide hydrolase in a buffered aqueous solution;

(c) adding test compounds to a plurality of containers;

(d) adding the mixture obtained in step (b) to said plurality of containers, and incubating the resulting mixtures of fluorescent probe, soluble epoxide hydrolase and test compounds;

(e) measuring the fluorescence polarization values of the incubated mixtures obtained in step (d) to obtain test fluorescence polarization values; and (f) determining the differences between the test fluorescence polarization values and the reference fluorescence polarization value;

wherein the differences in fluorescence polarization values obtained in step (f) indicate whether the test compounds inhibit soluble epoxide hydrolase.

Any of the conventional techniques and equipment known in the art for screening a large number of compounds (e.g., automated library screening) can be employed in this screening assay of the present invention. The plurality of containers used to hold the test compounds can take a variety of forms, for example, any of the conventionally used well plates for automated library screening. In one embodiment of the assay, the test compounds are diluted in a buffered aqueous solution prior to adding them to the plurality of containers. The general conditions, techniques, etc., employed in conducting this library screening assay are otherwise the same as discussed in detail above for the general assay method.

It should be understood that the foregoing Detailed Description and the following Examples are intended to be illustrative and not limiting with respect to the scope of the present invention. Various modifications and equivalents will become apparent to one skilled in the art, and the present invention as defined by the claims is intended to cover all such modifications and equivalents.

EXAMPLE 1

Synthesis of a Fluorescent Probe Labeled with Rhodamine:

A mixture of 1,12-diaminododecane 2 (0.11 $\mu$g) and 1 (commercially available from Molecular Probes, Inc.) (0.02 g) in dimethylformamide (2.5 mL) was stirred at room temperature for 4 days. The reaction mixture was fractionated directly over silica gel (eluent methylene chloride/ethanol 3/1 to ethanol/acetic acid 98/2 gradient) to give 3 (0.02 g).

A mixture of compound 3 (0.005 g), triethylamine (0.1 mL), and isopropylisocyanate (0.05 g) in dimethylformamide (1 mL) was stirred at room temperature for 3 days. Additional isopropylisocyanate (0.05 g) was added and stirring was continued for 3 hours. The solvent was removed under reduced pressure and the residue was fractionated over silica gel (chloroform/ethanol 4/1 to chloroform/ethanol/acetic acid 6/4/0/01) to give the product 4.

EXAMPLE 2

Fluorescence Polarization Assay to Determine Inhibition of sEH:

Step One: Characterization of the Fluorescent Probe

The wavelengths for maximum excitation and emission of the fluorescent probe should first be measured. An example of such a probe is compound (4), where these values are 529 nm and 565 nm, respectively. These fluorescence wavelength values were measured on an SLM-8100 fluorimeter with the probe dissolved in an assay buffer (20 mM TES, pH 7.0, 200 mM NaCl, 0.05% (w/v) CHAPS, 2 mM DTT).

Figure 1:
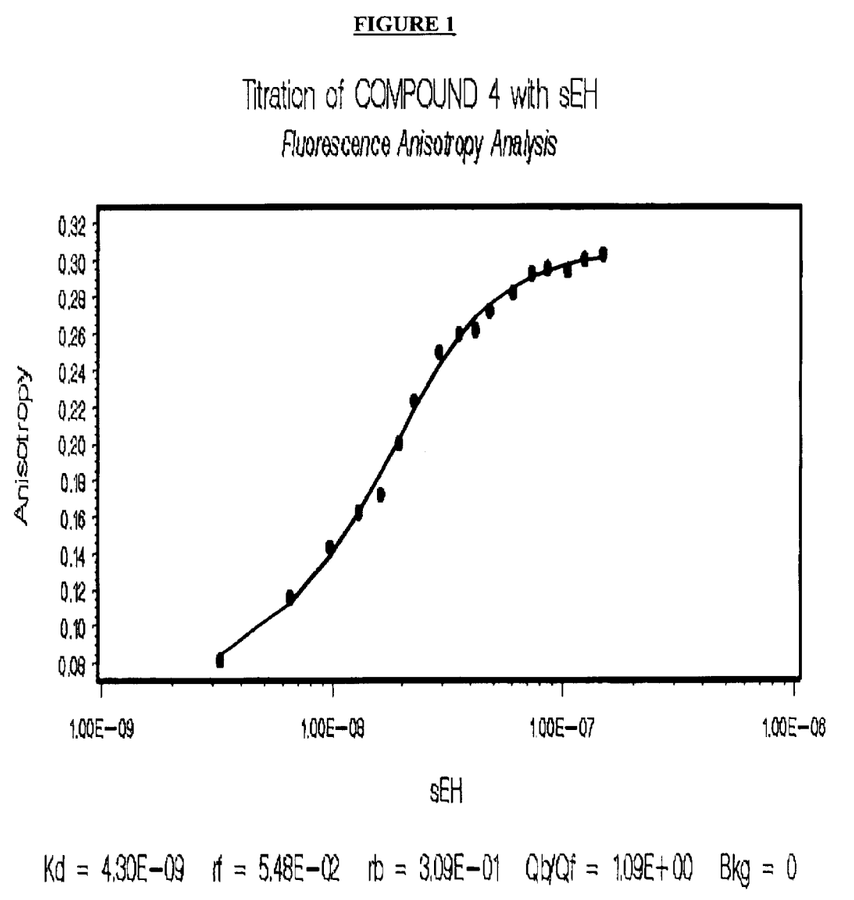
FIG. 1 shows the fluorescence polarization results obtained by titrating the fluorescent probe compound (4) with soluble epoxide hydrolase.

The affinity of the probe for sEH was then determined in a titration experiment. The fluorescence polarization value of compound 4 in assay buffer was measured on an SLM-8100 fluorimeter using the excitation and emission maximum values described above. Aliquots of sEH were added and fluorescence polarization was measured after each addition until no further change in polarization value was observed. Non-linear least squares regression analysis was used to calculate the dissociation constant of compound 4 from the polarization values obtained for sEH binding to compound 4. FIG. 1 shows the results from this titration experiment Step Two: Screening for Inhibitors of Probe Binding In order to screen a large number of compounds the assay was performed using a 96-well plate format. An example of such a plate is the Dynex Microfluor 1, low protein binding U-bottom black 96 well plates (# 7005). The plate is set up by first creating a complex between recombinant human sEH and a fluorescent probe that binds to the active site of sEH. In this example, the complex between compound 4 and sEH, was pre-formed in assay buffer (20 mM TES, pH 7.0, 200 mM NaCl, 0.05% (w/v) CHAPS, 1 mM TCEP). The concentrations of sEH and compound 4 in this solution were made up such that the final concentration in the assay was 10 nM sEH and 2.5 nM compound 4. Test compounds were then serially diluted into assay buffer, across a 96 well plate. The pre-formed sEH-probe complex was then added to all the wells and incubated for 15 minutes at room temperature. The fluorescence polarization was then measured using a fluorescence polarization plate reader set at the wavelengths appropriate for the fluorescent label on the fluorescent probe (4). In this example, an LJL Analyst was set to read rhodamine fluorescence polarization (Ex 530 nM, Em 580 nM). Non-linear least squares regression analysis was then used to calculate dissociation constants for the test compounds binding to sEH from the polarization values for the probe binding to sEH in the presence of the test compounds.

Figure 2:
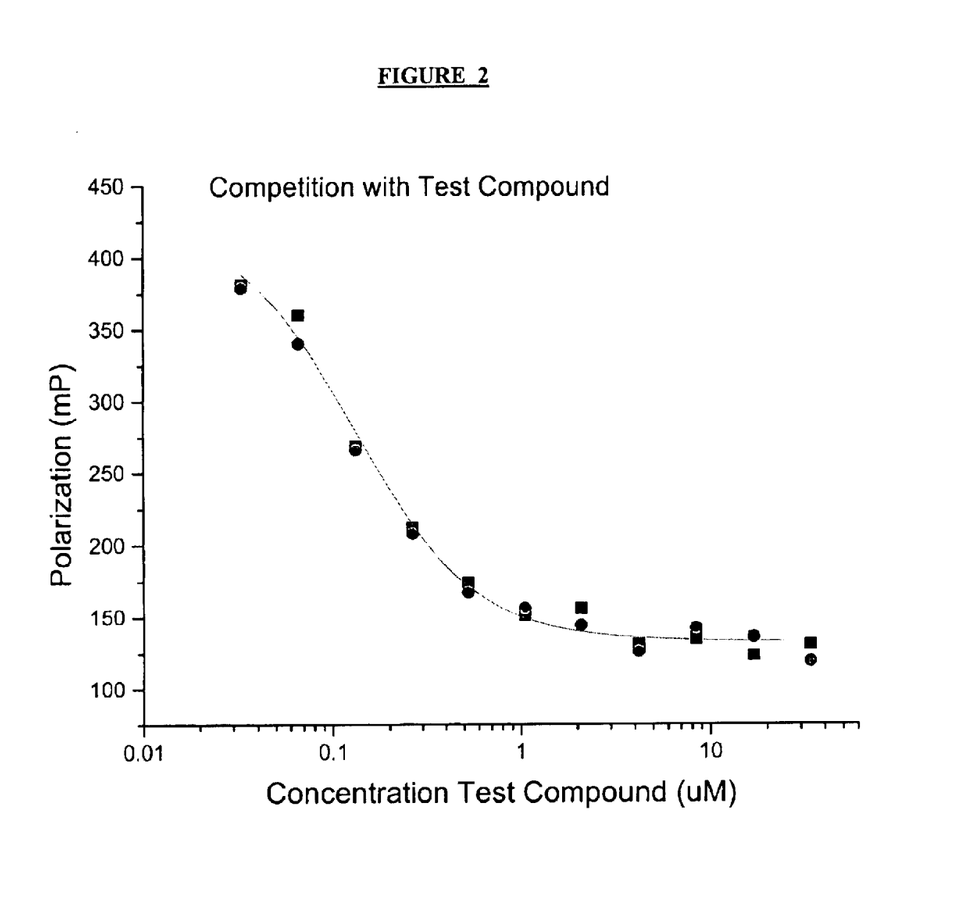
FIG. 2 shows the fluorescence polarization results obtained when screening a test compound for soluble epoxide hydrolase inhibitory activity at various dilutions using fluorescent probe compound (4) in an assay of the present invention.

FIG. 2 shows the results of this screening with an sEH inhibitory test compound at various serial dilutions. These results show a decrease in fluorescence polarization of the probe-sEH complex in the presence of the test compound, which is evidence that this test compound is a competitive inhibitor of soluble epoxide hydrolase that competes with the fluorescent probe for sEH active site binding.

What is claimed is:

1. A fluorescent probe that binds to the active site of soluble epoxide hydrolase, said probe having the formula (I):

X-spacer-$R_1$-Y       (I)

wherein X is the radical of compound that binds to the active site of soluble epoxide hydrolase, Y is a fluorescent label, "spacer" is a direct bond or is a $C_1$–$C_{16}$ alkylene group, a $C_2$–$C_{16}$ alkenylene group or a $C_2$–$C_{16}$ alkynylene group, wherein any of the available —$CH_2$— groups present in the $C_1$–$C_{16}$ alkylene group, $C_2$–$C_{16}$ alkenylene group or $C_2$–$C_{16}$ alkynylene group can optionally be replaced with O, $S(O)_p$ wherein p is 0 to 2, or $N(R_2)$, $R_1$ is selected from the group consisting of O, S, —N($R_2$)C(O)—, —C(O)N($R_2$)—, —N($R_2$)C(S)—, —C(S)N($R_2$)—, —N($R_2$)C(S)NH—, —NHC(S)N($R_2$), —N($R_2$)C(O)NH—, —NHC(O)N($R_2$), —$SO_2$N$R_2$—, —$NR_2SO_2$—, —$CH_2$N($R_2$)—, —N($R_2$)$CH_2$—, —$CH_2$S—, —$SCH_2$—, —C(O)$CH_2$S—, —SC(O)$CH_2$—, —$NHCH_2CH_2$S—, —$SCH_2CH_2$NH—, —NC(O)O—, —ONC(O)—, —C(O)O—, —OC(O)—, —NH—N=C($R_2$)—, —C($R_2$)=N—NH—, —NHCH($R_2$)—, —CH($R_2$)NH—, and $R_2$ is selected from H or $C_{1-3}$alkyl.

2. A fluorescent probe according to claim 1, wherein the probe binds to the active site of mammalian soluble epoxide hydrolase.

3. A fluorescent probe according to claim 2, wherein the probe binds to the active site of human soluble epoxide hydrolase or murine soluble epoxide hydrolase.

4. A fluorescent probe according to claim 1, having the following formula (II):

wherein:

$R_1$, Y and "spacer" are as defined in claim 1;

D is selected from N($R_4$), O or S;

E is selected from C(=Z), P(=Z) or S;

F is selected from N($R_5$), O, S, $CH_2$ or N($R_5$)C(O);

G is a direct bond or is $C_{1-6}$alkylene;

Z is O, S or N($R_7$);

$R_3$ is $C_{1-20}$alkyl, $C_{2-20}$alkenyl, $C_{2-20}$ alkynyl, $C_{3-10}$ cycloalkyl, $C_{5-7}$cycloalkenyl, $C_{1-6}$acyl, aryl, aryl-$C_{1-6}$alkyl, heteroaryl or heterocycle, each being optionally substituted with one or more $C_{1-3}$alkyl, halogen, CN, OH, $NH_2$, $C_{1-3}$alkyloxy, $C_{1-3}$alkylthio, $C_{1-3}$acyloxy, $C_{1-3}$acylthio, $C_{1-3}$alkylamino, $C_{1-3}$dialkylamino, $C_{1-3}$acylamino, $C_{1-3}$diacylamino or $C_{1-3}$alkyl($C_{1-3}$acyl)amino, $R_4$ and $R_5$ are independently selected from H or $C_{1-6}$alkyl, but at least one of $R_4$ and $R_5$ is hydrogen;

$R_6$ is selected from $C_{1-20}$alkylene, $C_{2-20}$ alkenylene, $C_{2-20}$ alkynylene, $C_{3-10}$cycloalkylene, $C_{5-7}$cycloalkenylene, $C_{1-6}$acyl, aryl, heteroaryl, heterocycle or a $C_{6-12}$ bridged carbocyclic ring system, optionally having one to three double bonds in the ring system, each being optionally substituted with one or more $C_{1-3}$alkyl, halogen, CN, OH, $NH_2$, $C_{1-3}$alkyloxy, $C_{1-3}$alkylthio, $C_{1-3}$acyloxy, $C_{1-3}$acylthio, $C_{1-3}$alkylamino, $C_{1-3}$dialkylamino, $C_{1-3}$acylamino, $C_{1-3}$diacylamino, $C_{1-3}$alkyl($C_{1-3}$acyl)amino or aryloxy; and $R_7$ is selected from H or $C_{1-6}$alkyl.

5. A fluorescent probe according to claim 4, having the following formula (III):

wherein:

Z is O or S; and $R_1$, $R_3$, $R_4$, $R_6$, F, G, "spacer" and Y are as defined in claim 4.

6. A fluorescent probe according to claim 5, wherein:

F is selected from N($R_5$) and O;

G is a direct bond or is $C_{1-3}$alkylene;

Z is O;

"spacer" is a $C_{1-6}$alkylene group;

$R_1$ is —N($R_2$)C(O)—, —C(O)N($R_2$)—, —N($R_2$)C(S)— or —C(S)N($R_2$)—, where $R_2$ is H or $C_{1-3}$alkyl;

$R_3$ is $C_{1-6}$alkyl, $C_{2-6}$ alkenyl, $C_{2-6}$ alkynyl, $C_{5-7}$ cycloalkyl, or phenyl, each being optionally substituted with one or more $C_{1-3}$alkyl, halogen, CN, $C_{1-3}$alkoxy or $C_{1-3}$alkylthio;

$R_4$ and $R_5$ are both hydrogen; and $R_6$ is selected from $C_{1-6}$alkylene, $C_{2-6}$ alkenylene, $C_{2-6}$ alkynylene, $C_{5-7}$cycloalkylene, phenyl or a $C_{6-12}$ bridged carbocyclic ring system, optionally having one to three double bonds in the ring system, each being optionally substituted with one or more $C_{1-3}$alkyl, halogen, CN, $C_{1-3}$alkoxy or $C_{1-3}$alkylthio.

7. A fluorescent probe according to claim 6, said probe having the following formula:

8. A fluorescent probe according to claim 1, wherein Y is a fluorescent label that fluoresces at a wavelength above about 450 nm.

9. A fluorescent probe according to claim 8, wherein the fluorescent label is selected from the group consisting of rhodamine and rhodamine derivatives, fluorescein and fluorescein derivatives, 4,4-difluor-4-bora-3a,4a-diaza-s-indacene and its derivatives, and cyanine dyes.

10. A fluorescent probe according to claim 9, wherein the fluorescent label is selected from the group consisting of rhodamine, tetramethyl rhodamine, carboxytetramethylrhodamine, carboxy-X-rhodamine, fluorescein, fluorinated fluoresceins, fluoresceinamine, carboxyfluorescein, alpha-iodoacetamidofluorescein, 4'-aminomethylfluorescein, 4'-N-alkylaminomethylfluorescein, 5-aminomethylfluorescein, 6-aminomethylfluorescein, 2,4-dichloro-1,3,5-triazin-2-yl-aminofluorescein, 4-chloro-6-methoxy-1,3,5-triazin-2-yl-aminofluorescein, fluoresceinisothiocyanate, 4,4-difluor-4-bora-3a,4a-diaza-s-indacene and its derivatives and cyanine dyes.

11. A method for preparing the fluorescent probe of formula (II) according to claim 4 wherein $R_1$ is —N($R_2$)C(O)—, D is —N($R_4$)—, E is —C(=Z)— and F is N($R_5$), said method comprising steps (a) and (b1) or steps (a) and (b2):

(a) reacting a compound of formula (IV) with a compound of formula (V) under coupling conditions to produce a compound of formula (VI):

and (b1) reacting a compound of formula VI produced in step (a) with an isocyanate $R_3N=C=O$ or an isothiocyanate $R_3N=C=S$, in the presence of a base in an inert solvent, to produce a compound of formula IIa:

or (b2) reacting a compound of formula (VI) produced in step (a) with a carbamoyl chloride $R_3R_4N(C=O)Cl$ where $R_4$ is $C_{1-6}$alkyl or a thiocarbamoyl chloride $R_3R_4N(C=S)Cl$ where $R_4$ is $C_{1-6}$alkyl, in the presence of a base in an inert solvent, to produce a compound of formula IIb where $R_4$ is $C_{1-6}$alkyl;

wherein, except where otherwise noted above, Y, G, spacer, Z, $R_2$, $R_3$, $R_4$, $R_5$ and $R_6$ are as defined in claim 4.

12. A fluorescence polarization assay for determining whether a compound inhibits soluble epoxide hydrolase, said assay comprising:
   (a) determining the fluorescence polarization values of a fluorescent probe according to claim 1 and said fluorescent probe bound to soluble epoxide hydrolase to obtain a range of fluorescence polarization values and selecting a reference fluorescence polarization value falling within that range;
   (b) mixing the fluorescent probe with soluble epoxide hydrolase in a buffered aqueous solution;
   (c) mixing a test compound with the mixture obtained in step (b) and incubating the resulting mixture of fluorescent probe, soluble epoxide hydrolase and test compound;
   (d) measuring the fluorescence polarization value of the incubated mixture obtained in step (c) to obtain a test fluorescence polarization value; and
   (e) determining the difference between the test fluorescence polarization value and the reference fluorescence polarization value;
   wherein the difference in fluorescence polarization values obtained in step (e) indicates whether the test compound inhibits soluble epoxide hydrolase.

13. An assay according to claim 12, wherein the range of fluorescence polarization values in step (a) is obtained by periodically adding increasing amounts of soluble epoxide hydrolase to an amount of fluorescent probe in a buffered aqueous solution and periodically measuring the fluorescence polarization value of this mixture.

14. An assay according to claim 12, wherein the reference fluorescence polarization value is selected such that the difference between the reference fluorescence polarization value and the polarization value of free fluorescent probe is equal to about 50% to 100% of the difference between the polarization value of fluorescent probe bound to soluble epoxide hydrolase and the polarization value of free fluorescent probe.

15. The assay according to claim 12, wherein the difference in fluorescence polarization values obtained in step (e) is a positive value.

16. The assay according to claim 12, wherein the difference in fluorescence polarization values obtained in step (e) is a negative value.

17. The assay according to claim 12, wherein the soluble epoxide hydrolase is mammalian soluble epoxide hydrolase.

18. The assay according to claim 17, wherein the soluble epoxide hydrolase is human or murine soluble epoxide hydrolase.

19. The assay according to claim 12, wherein the fluorescent probe has the following formula (II):

$$R_3\text{-}D\text{-}E\text{-}F\text{-}G\text{-}R_6\text{-spacer-}R_1\text{-}Y \quad (II)$$

wherein:
   Y is a fluorescent label;
   "spacer" is a direct bond or is a $C_1$–$C_{16}$alkylene group, a $C_2$–$C_{16}$alkenyl group or a $C_2$–$C_{16}$alkynylene group, wherein any of the available —$CH_2$— groups present in the $C_1$–$C_{16}$alkylene group, $C_3$–$C_{16}$alkenylene group or $C_2$–$C_{16}$alkynylene group can optionally be replaced with O, $S(O)_p$ wherein p is 0 to 2, or $N(R_2)$;
   $R_1$ is selected from the group consisting of O, S, —$N(R_2)$C(O)—, —C(O)N($R_2$)—, —N($R_2$)C(S)—, —C(S)N($R_2$)—, —N($R_2$)C(S)NH—, —NHC(S)N($R_2$)C(O)NH—, —NHC(O)N($R_2$), —$SO_2NR_2$—, —$NR_2SO_2$—, —$CH_2N(R_2)$—, —$CH_2S$—, —$SCH_2$—, —C(O)$CH_2S$—, —SC(O)$CH_2$—,

[two maleimide-like structures shown]

—$NHCH_2CH_2S$—, —$SCH_2CH_2NH$—, —NC(O)O—, —ONC(O)—, —C(O)O—, —OC(O)—, —NH—N=C($R_2$)—, —C($R_2$)=N=NH—, —NHCH($R_2$)—, —CH($R_2$)NH—, and $R_2$ is selected from H or $C_{1-3}$alkyl;
   D is selected from N($R_4$), O or S;
   E is selected from C(=Z), P(=Z) or S;
   F is selected from N($R_5$), O, S, $CH_2$ or N($R_5$)C(O);
   G is a direct bond or is $C_{1-6}$alkylene;
   Z is O, S or N($R_7$);
   $R_3$ is $C_{1-20}$alkyl, $C_{2-20}$alkenyl, $C_{2-20}$alkynyl, $C_{3-10}$cycloalkyl, $C_{5-7}$cycloalkenyl, $C_{1-6}$acyl, aryl, aryl-$C_{1-6}$alkyl, heteroaryl or heterocycle, each being optionally substituted with one or more $C_{1-3}$alkyl, halogen, CN, OH, $NH_2$, $C_{1-3}$alkyloxy, $C_{1-3}$alkylthio, $C_{1-3}$acyloxy, $C_{1-3}$acylthio, $C_{1-3}$alkylamino, $C_{1-3}$dialkylamino, $C_{1-3}$acylamino, $C_{1-3}$diacylamino or $C_{1-3}$alkyl($C_{1-3}$acyl)amino,
   $R_4$ and $R_5$ are independently selected from H or $C_{1-6}$alkyl, but at least on of $R_4$ and $R_5$ is hydrogen;
   $R_6$ is selected from $C_{1-20}$alkylene, $C_{2-20}$alkenylene, $C_{2-20}$alkynylene, $C_{3-10}$cycloalkylene, $C_{5-7}$cycloalkenylene, $C_{1-6}$acyl, aryl, heteroaryl, heterocycle or a $C_{6-12}$ bridged carbocyclic ring system, optionally having one to three double bonds in the ring system, each being optionally substituted with one or more $C_{1-3}$alkyl, halogen, CN, OH, $NH_2$, $C_{1-3}$alkyloxy, $C_{1-3}$alkylthio, $C_{1-3}$acyloxy, $C_{1-3}$acylthio, $C_{1-3}$alkylamino, $C_{1-3}$dialkylamino, $C_{1-3}$acylamino, $C_{1-3}$diacylamino, $C_{1-3}$alkyl($C_{1-3}$acyl)amino or aryloxy; and
   $R_7$ is selected from H or $C_{1-6}$alkyl.

20. The assay according to claim 19, wherein the fluorescent probe has the following formula (III):

$$R_3\text{-}N(R_4)\text{-}C(=Z)\text{-}F\text{-}G\text{-}R_6\text{-spacer-}R_1\text{-}Y \quad (III)$$

wherein:
   Z is O or S; and
   $R_1$, $R_3$, $R_4$, $R_6$, F, G, "spacer" and Y are as defined in claim 19.

21. The assay according to claim 20, wherein the fluorescent probe has the following formula:

22. An assay for screening a library of test compounds to determine whether the compounds inhibit soluble epoxide hydrolase, said assay comprising:
(a) determining the fluorescence polarization values of a fluorescent probe according to claim 1 and said fluorescent probe bound to soluble epoxide hydrolase to obtain a range of fluorescence polarization values and selecting a reference fluorescence polarization value falling within that range;
(b) mixing the fluorescent probe with soluble epoxide hydrolase in a buffered aqueous solution;
(c) adding test compounds to a plurality of containers;
(d) adding the mixture obtained in step (b) to said plurality of containers, and incubating the resulting mixtures of fluorescent probe, soluble epoxide hydrolase and test compounds;
(e) measuring the fluorescence polarization values of the incubated mixtures obtained in step (d) to obtain test fluorescence polarization values; and
(f) determining the differences between the test fluorescence polarization values and the reference fluorescence polarization value;
wherein the differences in fluorescence polarization values obtained in step (f) indicate whether the test compounds inhibit soluble epoxide hydrolase.

23. An assay according to claim 22, wherein the range of fluorescence polarization values in step (a) is obtained by periodically adding increasing amounts of soluble epoxide hydrolase to an amount of fluorescent probe in buffered aqueous solution and periodically measuring the fluorescence polarization value of this mixture.

24. An assay according to claim 22, wherein the reference fluorescence polarization value is selected such that the difference between the reference fluorescence polarization value and the polarization value of free fluorescent probe is equal to about 50% to 100% of the difference between the polarization value of fluorescent probe bound to soluble epoxide hydrolase and the polarization value of free fluorescent probe.

25. The assay according to claim 22, wherein at least some of the differences in fluorescence polarization values obtained in step (f) are positive values.

26. The assay according to claim 22, wherein at least some of the differences in fluorescence polarization values obtained in step (f) are negative values.

27. The assay according to claim 22, wherein the soluble epoxide hydrolase is mammalian soluble epoxide hydrolase.

28. The assay according to claim 27, wherein the soluble epoxide hydrolase is human or murine soluble epoxide hydrolase.

29. The assay according to claim 22, wherein the fluorescent probe has the following formula (II):

$$R_3\diagdown_D\diagup^E\diagdown_F\diagup^G\diagdown_{R_6}\diagup\text{spacer}—R_1—Y \quad (II)$$

wherein:
Y is a fluorescent label;
"spacer" is a direct bond or is a $C_1$–$C_{16}$alkylene group, a $C_2$–$C_{16}$alkenyl group or a $C_2$–$C_{16}$alkynylene group, wherein any of the available —$CH_2$— groups present in the $C_1$–$C_{16}$alkylene group, $C_3$–$C_{16}$alkenylene group or $C_2$–$C_{16}$alkynylene group can optionally be replaced with O, $S(O)_p$ wherein p is 0 to 2, or $N(R_2)$;
$R_1$ is selected from the group consisting of O, S, —$N(R_2)$C(O)—, —C(O)$N(R_2)$—, —$N(R_2)$C(S)—, —C(S)N$(R_2)$—, —$N(R_2)$C(S)NH—, —NHC(S)N$(R_2)$C(O)NH—, —NHC(O)N$(R_2)$, —$SO_2NR_2$—, —$NR_2SO_2$—, —$CH_2N(R_2)$—, —$CH_2S$—, —$SCH_2$—, —C(O)$CH_2S$—, —$SC(O)CH_2$—,

[two maleimide structures with —S— substituents]

—$NHCH_2CH_2S$—, —$SCH_2CH_2NH$—, —NC(O)O—, —ONC(O)—, —C(O)O—, —OC(O)—, —NH—N=C($R_2$)—, —C($R_2$)=N=NH—, —NHCH($R_2$)—, —CH($R_2$)NH—, and $R_2$ is selected from H or $C_{1-3}$alkyl;
D is selected from $N(R_4)$, O or S;
E is selected from C(=Z), P(=Z) or S;
F is selected from $N(R_5)$, O, S, $CH_2$ or $N(R_5)C(O)$;
G is a direct bond or is $C_{1-6}$alkylene;
Z is O, S or $N(R_7)$;
$R_3$ is $C_{1-20}$alkyl, $C_{2-20}$alkenyl, $C_{2-20}$alkynyl, $C_{3-10}$cycloalkyl, $C_{5-7}$cycloalkenyl, $C_{1-6}$acyl, aryl, aryl-$C_{1-6}$alkyl, heteroaryl or heterocycle, each being optionally substituted with one or more $C_{1-3}$alkyl, halogen, CN, OH, $NH_2$, $C_{1-3}$alkyloxy, $C_{1-3}$alkylthio, $C_{1-3}$acyloxy, $C_{1-3}$acylthio, $C_{1-3}$alkylamino, $C_{1-3}$dialkylamino, $C_{1-3}$acylamino, $C_{1-3}$diacylamino or $C_{1-3}$alkyl($C_{1-3}$acyl)amino, $R_4$ and $R_5$ are independently selected from H or $C_{1-6}$alkyl, but at least on of $R_4$ and $R_5$ is hydrogen;

$R_6$ is selected from $C_{1-20}$alkylene, $C_{2-20}$alkenylene, $C_{2-20}$alkynylene, $C_{3-10}$cycloalkylene, $C_{5-7}$cycloalkenylene, $C_{1-6}$acyl, aryl, heteroaryl, heterocycle or a $C_{6-12}$ bridged carbocyclic ring system, optionally having one to three double bonds in the ring system, each being optionally substituted with one or more $C_{1-3}$alkyl, halogen, CN, OH, $NH_2$, $C_{1-3}$alkyloxy, $C_{1-3}$alkylthio, $C_{1-3}$acyloxy, $C_{1-3}$acylthio, $C_{1-3}$alkylamino, $C_{1-3}$dialkylamino, $C_{1-3}$acylamino, $C_{1-3}$diacylamino, $C_{1-3}$alkyl($C_{1-3}$acyl)amino or aryloxy; and $R_7$ is selected from H or $C_{1-6}$alkyl.

30. The assay according to claim 29, wherein the fluorescent probe has the following formula (III):

(III)

wherein:

Z is O or S; and $R^1$, $R^3$, $R^4$, $R^6$, F, G, "spacer" and Y are as defined in claim 29.

31. The assay according to claim 30, wherein the fluorescent probe has the following formula:

* * * * *